United States Patent
Sayet et al.

(10) Patent No.: US 7,476,195 B2
(45) Date of Patent: Jan. 13, 2009

(54) BODY FLUID FLOW CONTROL DEVICE

(75) Inventors: Peter H. Sayet, Fort Lauderdale, FL (US); Lloyd A. Sutherland, Boca Raton, FL (US); Victor Politano, North Miami, FL (US)

(73) Assignee: Precision Medical Devices, Inc., Ft. Lauderdale, FL (US)

( * ) Notice: Subject to any disclaimer, the term of this patent is extended or adjusted under 35 U.S.C. 154(b) by 702 days.

(21) Appl. No.: 10/776,034

(22) Filed: Feb. 10, 2004

(65) Prior Publication Data

US 2004/0249241 A1    Dec. 9, 2004

Related U.S. Application Data

(60) Division of application No. 09/965,762, filed on Sep. 28, 2001, now Pat. No. 6,689,046, which is a continuation-in-part of application No. 09/676,336, filed on Sep. 29, 2000, now Pat. No. 6,527,701.

(51) Int. Cl.
*A61F 2/02* (2006.01)
*A61B 17/08* (2006.01)

(52) U.S. Cl. .................. 600/30; 623/23.66; 623/26; 606/151

(58) Field of Classification Search ............. 600/29–32, 600/38; 128/897–899, DIG. 25; 606/151; 623/23.64–23.67, 26
See application file for complete search history.

(56) References Cited

U.S. PATENT DOCUMENTS

| | | |
|---|---|---|
| 3,419,008 A | 12/1968 | Plishner |
| 3,815,576 A | 6/1974 | Balaban |
| 3,854,469 A | 12/1974 | Giori et al. |
| 3,924,631 A | 12/1975 | Mancusi, Jr. |
| 3,926,175 A | 12/1975 | Allen et al. |
| 4,024,855 A | 5/1977 | Bucalo |
| 4,258,705 A | 3/1981 | Sorensen et al. |
| 4,453,436 A | 6/1984 | Tokuno |
| 4,643,169 A | 2/1987 | Koss et al. |
| 4,800,900 A | 1/1989 | French |
| 4,994,019 A | 2/1991 | Fernandez et al. |
| 4,994,020 A | 2/1991 | Polyak |
| 5,163,897 A | 11/1992 | Persky |
| 5,509,888 A | 4/1996 | Miller |
| 5,562,598 A | 10/1996 | Whalen et al. |
| 5,704,893 A | 1/1998 | Timm |
| 6,074,341 A | 6/2000 | Anderson et al. |
| 6,095,969 A | 8/2000 | Karram et al. |

(Continued)

*Primary Examiner*—John P Lacyk
(74) *Attorney, Agent, or Firm*—Robert C. Kain, Jr.

(57) ABSTRACT

An implantable apparatus and a method for controlling fluid flow within a host body, for example for use as an incontinence device. A constricting member is provided for reducing fluid flow within a body canal when in a closed position, and for allowing fluid flow within the body canal when in an open position. In addition, there is a control mechanism for controlling movement of the constricting member between said open and closed positions. A link member links the constricting member and the control mechanism such that the constricting member and the control mechanism are implantable in different parts of the host body. A coupling for selectively transmitting axial movement to the link member may be provided between the link member and the control mechanism so that the constricting member cannot apply a damaging amount of force to the body canal.

18 Claims, 8 Drawing Sheets

U.S. PATENT DOCUMENTS

| | | |
|---|---|---|
| 6,135,945 A | 10/2000 | Sultan |
| 6,210,347 B1 | 4/2001 | Forsell |
| 7,223,228 B2 | 5/2007 | Timm et al. |

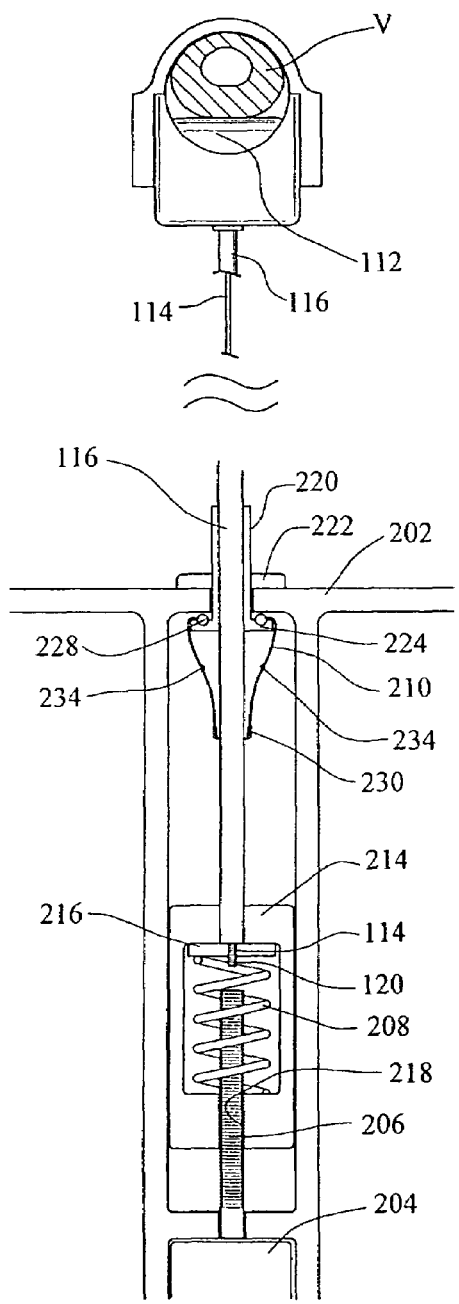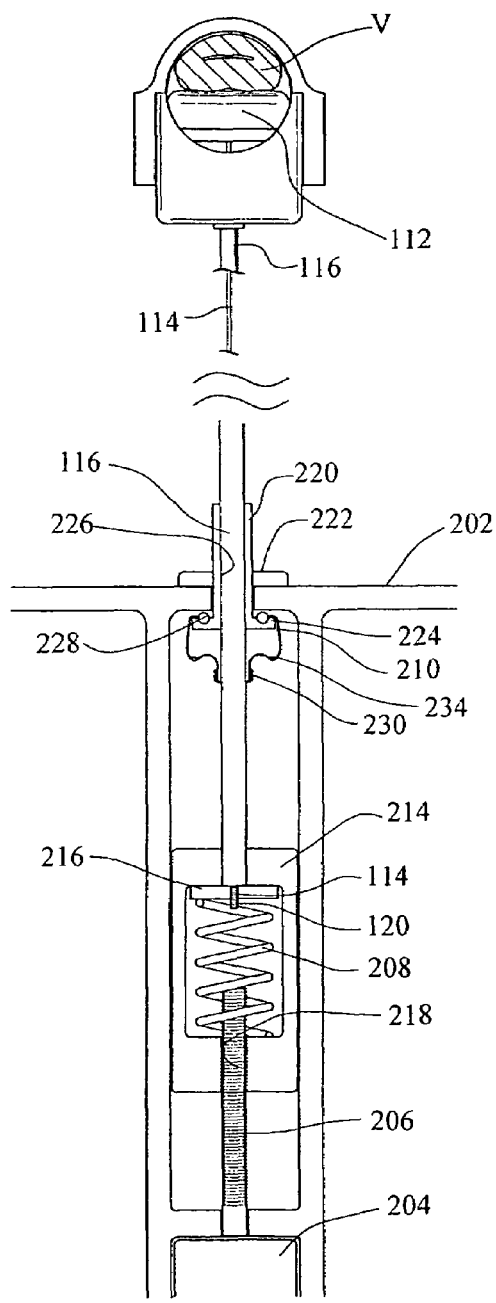

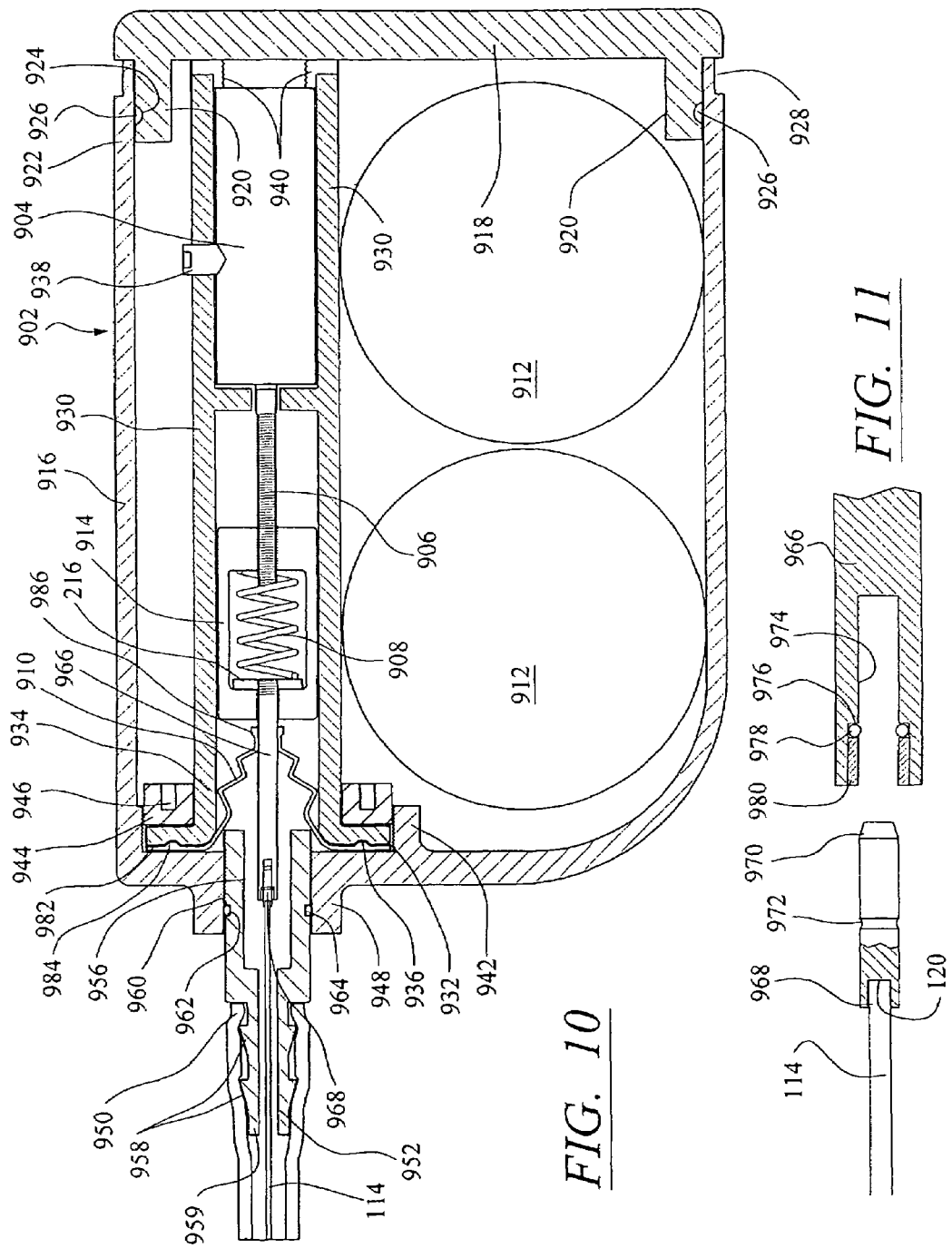

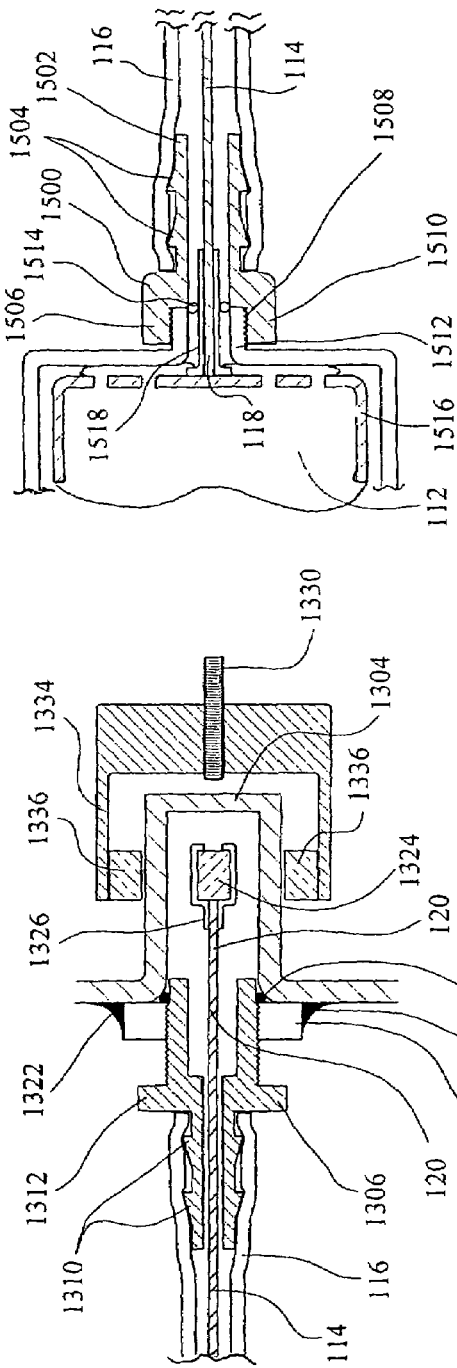
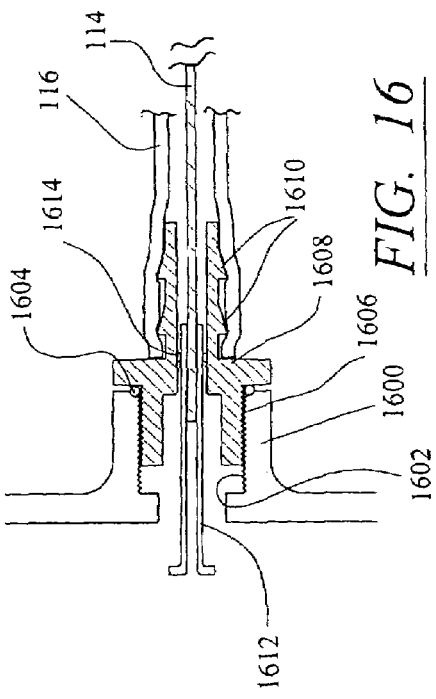
FIG. 14
FIG. 15
FIG. 16

BODY FLUID FLOW CONTROL DEVICE

CROSS-REFERENCE TO RELATED APPLICATIONS

This is a divisional application of U.S. patent application Ser. No. 09/965,762, filed Sep. 28, 2001, now U.S. Pat. No. 6,689,046, which is a continuation-in-part application of U.S. patent application Ser. No. 09/676,336, filed Sep. 29, 2000, now U.S. Pat. No. 6,527,701.

FIELD OF THE INVENTION

The invention relates to an implantable medical device and a method for the control of fluid flow through a body host canal or vessel, such as a urethra.

BACKGROUND

Incontinence is a condition wherein persons lose control over their voluntary urinary function. The condition can arise from various causes, which include a variety of related and unrelated diseases, aging, and deterioration of the voluntary urethra sphincter muscle. The cost and inconvenience to persons suffering from this condition are great. Several remedies exist that are known in the prior art. Among these, the most common are surgical corrections both minor and major, drugs, devices and diaper capture systems which serve to capture discharges. Another solution is to place a patch over the urinary orifice to prevent unwanted discharge. Possibly, the most effective solution to date is the use of an artificial sphincter. This device is surgically installed and is hydraulically or pneumatically driven, operating by inflation of ballasts to suppress fluid flow. However, control of this device is sometimes difficult and is often inconvenient. Throughout the full range of the available treatment alternatives, the levels of efficacy, useful life, and complications vary greatly, with none of the current treatment alternatives being particularly effective in especially severe cases. Accordingly, there is a need for an improved apparatus to control the loss of voluntary urinary function.

SUMMARY OF THE INVENTION

The present invention overcomes and alleviates the above-mentioned drawbacks and disadvantages in the art through novel implantable body fluid flow control devices for the control of fluid flow through a host body canal or vessel, such as a urethra.

Generally speaking, and in accordance with a first aspect of the invention, an implantable apparatus for controlling fluid flow within a host body comprises a constricting member for allowing fluid flow within a body canal when in an open position and for reducing fluid flow within a body canal when in a closed position, an actuating member for operating the constricting member between said open and closed positions, and control means for operating said actuating member.

Preferably, the constricting member comprises a first engaging element and a second engaging element for coupling to the first engaging element to encircle a body canal. At least one of the first engaging element and the second engaging element preferably has apertures to allow tissue growth therethrough from and to the surface of the body canal. A locking member is preferably provided for locking the first engaging element and second engaging element into the locked position.

The constricting member preferably comprises a plunging member moveable such that the plunging member may apply pressure against said body canal to compress said body canal into said closed position. The actuating member preferably comprises a connector having first and second ends. The first end of the connector is preferably attached to said plunging member and is axially moveable by said control means to move said plunging member.

The actuating member may comprise a housing whereby the second end of the connector extends slidably through an aperture in the housing and is coupled to an actuator provided in the housing, for example physically or by way of magnetic fields, such that movement of the actuator results in movement of said plunging member away from the body canal to allow at least some fluid flow therethrough. The actuating member preferably comprises a motor operatively coupled to the second end of the connector so that activation of the motor causes the second end of the connector to be axially pulled towards the motor resulting in movement of said plunging member away from the body canal to allow at least some fluid flow therethrough.

A trigger mechanism is preferably provided for activating the motor. The trigger mechanism may be a magnetically operated switch, a radio-controlled circuit, a manually operated button implanted under the patient's skin, or any other suitable trigger mechanism. A manual override system may also be included. The manual override system may include a magnet that can be used outside the patient's body.

A second aspect of the invention provides an implantable apparatus for controlling fluid flow within a host body comprising a constricting member for restricting fluid flow within a body canal when in a closed position, and for allowing fluid flow within the body canal when in an open position; a control mechanism for controlling movement of the constricting member between said open and closed positions; and a link member linking the constricting member and the control mechanism such that the constricting member and the control mechanism are implantable in different parts of the host body.

The control mechanism can be separable from said link member so that said control mechanism may be replaced without removal of the constricting member or the link member from the host body.

Preferably, the link member is adapted for moving said constricting member between said open and closed positions so as to alter fluid flow within the body canal, and an actuating member is preferably provided for actuating said link member. The link member may be a cable provided in a protective sleeve, or may be any other suitable link between the constricting member and the control member such as a wire carrying electronic control signals, a wireless radio communication system, etc.

The actuating member and the control mechanism are preferably provided in a housing separate from the constricting member. The actuating member is preferably a motor, most preferably with a remotely operated trigger mechanism, for example, a magnetically operated trigger mechanism, for activating the motor or magnetic unit from a position outside the patient's body.

The motor or magnetic unit preferably acts through a worm gear. Preferably, the worm gear defines an axis, and the link member is attached to a casing, the worm gear co-operating with a threaded aperture provided in said casing in order to move said casing in a direction parallel to the axis of the worm gear.

According to another aspect of the present invention, there is provided a seal for an elongated link member, the link member extending between an implantable apparatus for implantation in a host body and a control mechanism. The link member extends through an opening in a housing. The seal includes a tubular membrane having two openings, one opening being sealed to the housing, the other opening being sealed to the link member such that fluid entering the housing around the link member is trapped by the membrane. The membrane flexes to allow movement of the shaft.

The membrane is preferably sealed to said link member by gripping means extending around the membrane and the shaft. The gripping means may comprise a coil. The membrane preferably comprises a bellows that folds inwardly when the link member is moved axially away from an interior of the housing, and expands when the link member is moved axially into the housing. The bellows may include a reinforcing ring so that folding of the bellows may be controlled.

According to yet another aspect of the invention, there is provided an operating mechanism for a constricting member for controlling fluid flow in a body canal. The constricting member is actuable between open and closed positions. The operating mechanism includes an axially moveable link member operatively connected to the constricting member for actuating the constricting member. Operating means are provided for axially moving the link member. A coupling for selectively transmitting the axial movement is connected between the link member and the operating means.

The coupling acts so that in one direction there is positive engagement between the operating means and the link member, whereas in an other direction, some play is allowed between the operating means and the link member. The coupling may be used so that opening of the body canal may be achieved by direct actuation of the operating means acting on the link member, but on closing of the body canal, the coupling prevents pressure being directly applied to the body canal by the operating means, thus reducing the likelihood of damage to the body canal.

The coupling may include magnets or a compressible member. A magnet may be attached to the link member, and at least one other magnet may be attached to the operating means. The magnets may be physically moveable towards and away from each other, or they may be electromagnets such that they may be operated when required. The compressible member may be provided in a moveable casing. The link member may be operatively connected to the compressible member, the motor acting to move the casing, and the compressible member acting to move the link member. Alternatively, the coupling may include chain links or a jointed extensible framework, or other means of preventing direct application of pressure to the body canal.

In the case of a coupling comprising magnets, a manual override system may be included, which manual override system comprises a further magnet operable from outside the patient's body. The manual override magnet should be of sufficient strength to move the magnet attached to the link member against the magnetic force of the magnet attached to the operating means.

Another aspect of the invention provides a method of controlling fluid flow within a host body. The method includes implanting a constricting member around a body canal, the constricting member reducing fluid flow in the body vessel when in a closed position. The method further includes implanting a control mechanism in the host body; and providing and implanting a link member between the constricting member and the control mechanism to allow the control mechanism to control the constricting member. The control mechanism may be removed from the host body and replaced without removal of the constricting member and the linking member.

The constricting member may include engaging elements defining an opening therebetween, the method including surrounding the body canal with the engaging elements so that the body canal extends through the opening.

The method may further include suturing the engaging elements to the vessel. In addition, the control mechanism may be implanted remote from the body canal.

Yet a further aspect of the invention includes a remote telemetry system for an implantable apparatus, the telemetry system including a signaling mechanism capable of sending and receiving signals to and from a control unit implanted in a host body in order to monitor the operation of the implantable apparatus, the telemetry system being capable of altering operating settings of the implantable apparatus.

The signals are preferably electromagnetic radiation, most preferably radio signals. The implantable apparatus may include sensors to monitor actions of the implantable apparatus on the host body, and the telemetry system would include a mechanism to interrogate the sensors to provide feedback on the sensed data. Preferably, the sensors are capable of monitoring pressure exerted by a moveable part of the implantable apparatus on a part of the host body, the feedback on the sensed data including commands to alter the range of movement of the moveable part of the implantable apparatus.

Another aspect of the invention includes an implantable apparatus for controlling fluid flow in a host body. The implantable apparatus includes a constricting mechanism including a reciprocable member for selectively applying pressure to a canal of the host body in order to selectively constrict the canal. A pressure sensor is included for detecting the pressure applied by the reciprocable member to the canal. A feedback system is also included for altering movement of said reciprocable member in response to the pressure sensed by said pressure sensor in order to prevent damage to said canal.

The object and advantages of the implantable fluid flow control devices of the present invention permit implantation and use without severing the canal or vessel to be constricted. Moreover, because trauma is minimized with respect to the canal or vessel, and the devices of the present invention are relatively small, lightweight and made of corrosion-resistant material, such as durable plastics, titanium or stainless steel, the devices are suitable for use for extended periods of time to control fluid flow through numerous types of vessels to control, for example, urination, defecation, ejaculation, nutrition absorption for control of obesity, etc. Splitting the fluid flow control device and its control box also provides significant advantages. The surgery to implant the fluid flow control device is delicate and involved, whereas the surgery to implant the control box is much less involved as the control box may be implanted in an easily accessible place, just under the skin of the patient. Thus, when any part of the control box fails, the control box may be removed and replaced with a new control box without needing to adjust the fluid flow control device. The replacement of the control box does not therefore need to be done by a specialist surgeon, and may be performed in a large number of hospitals or even physicians offices under local anaesthetic. The surgery is thus much less traumatic for the patient and may be performed in a location that is convenient for the patient rather than in a hospital that is able to perform specialized urological surgeries.

These and other objects, features and advantages of the present invention may be better understood and appreciated from the following detailed description of the embodiments thereof, selected for purposes of illustration and shown in the accompany drawings. It should therefore be understood that the particular embodiments illustrating the present invention are exemplary only and not to be regarded as limitations of the present invention. In particular, the illustrated embodiment relates to an artificial sphincter for a urethra, but it should be understood that the device can be used with any body fluid flow canal or vessel.

BRIEF DESCRIPTION OF THE DRAWINGS

The foregoing and other objects, advantages and features of the present invention, and the manner in which the same are accomplished, will become more readily apparent upon consideration of the following detailed description of the present invention taken in conjunction with the accompany drawings which illustrate a preferred and exemplary embodiment, and wherein:

FIG. 7 is a partial cross-sectional view of a motorized activating member for use with the device of FIG. 1 in the open position;

FIG. 8 is a partial cross-sectional view of the motorized activating member of FIG. 7 in an intermediate position;

FIG. 10 is a top partial cross-sectional view of an alternative embodiment of control box and device;

FIG. 11 is an enlarged cross-sectional view of the joint between the cable and link member of FIG. 10;

FIG. 14 is a partial cross-sectional view of the control device of FIG. 13;

FIG. 15 is a partial cross-sectional view of an alternative means of connecting a link member to a body fluid flow control device; and FIG. 16 is a partial cross-sectional view of a further alternative means of connecting a link member to a body fluid flow control device.

DETAILED DESCRIPTION OF THE INVENTION

Figure 1:
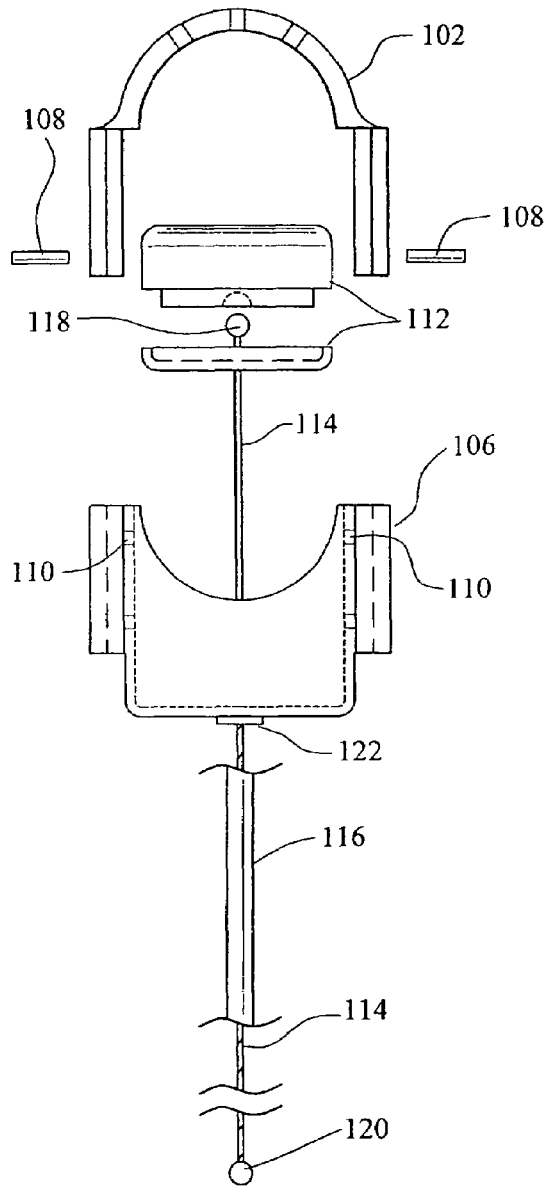
FIG. 1 is a front exploded view of a body fluid flow control device according to the invention.
Figure 2:
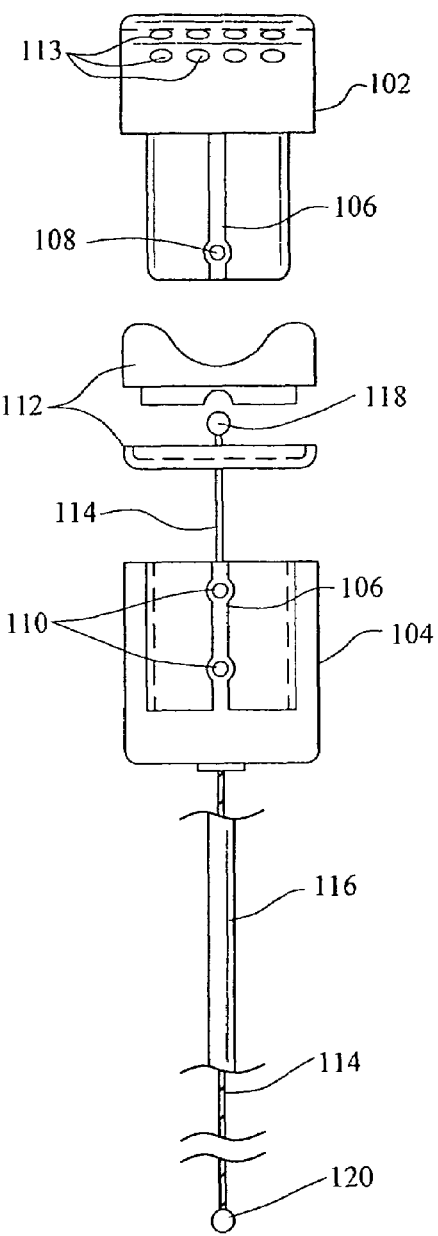
FIG. 2 is a side exploded view of the body fluid flow control device of FIG. 1.
Figure 3:
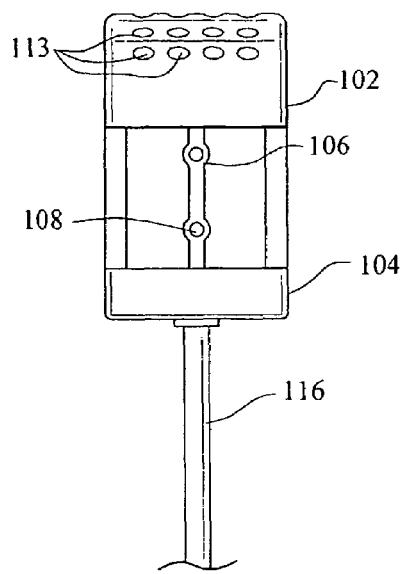
FIG. 3 is a partial side view of the device of FIG. 1 in the closed position.
Figure 4:
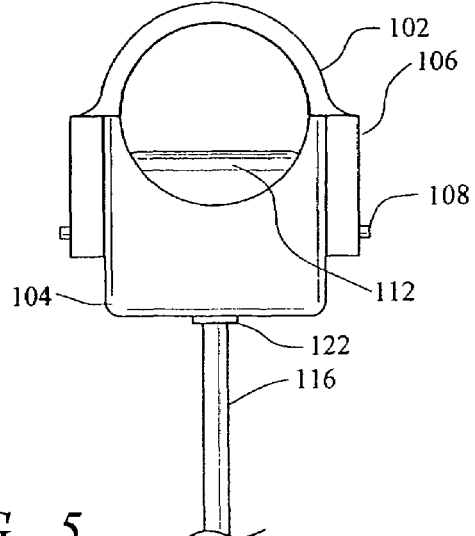
FIG. 4 is a partial front view of the device of FIG. 1 in the closed position.
Figure 5:
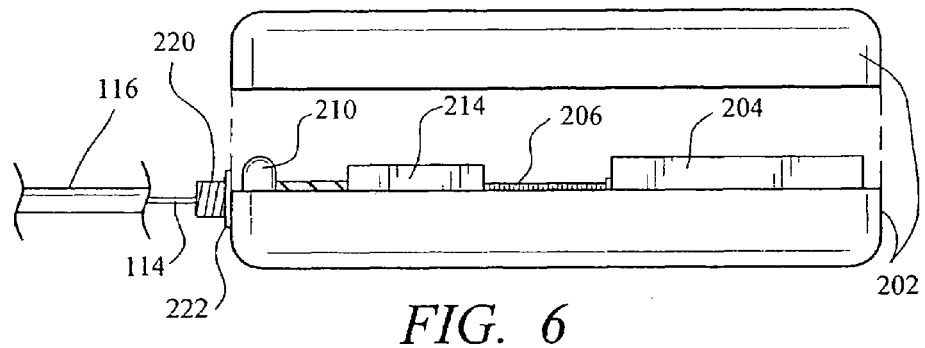
FIG. 5 is a side exploded view of a control box and device for use with a body fluid flow control device.
Figure 6:
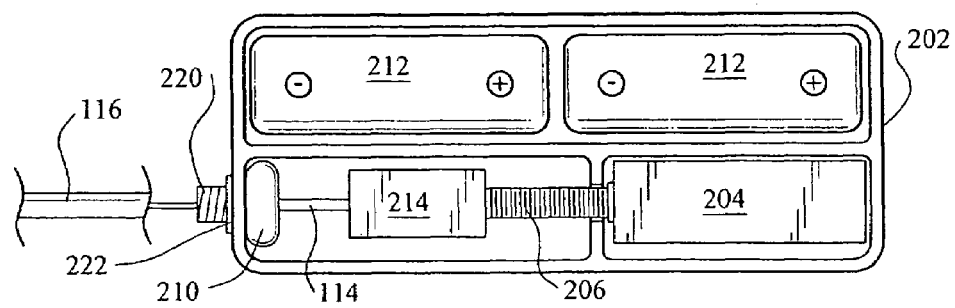
FIG. 6 is a partial top view of the control box and device of FIG. 5.

By way of illustrating and providing a more complete appreciation of the present invention and many of the attendant advantages thereof, the following detailed description is given concerning the novel implantable body fluid control device and uses thereof.

Referring now in more detail to the drawings, in which like numerals refer to like parts throughout several views, FIGS. 1-4 show a body fluid flow control device according to the present invention. The body fluid flow control device comprises a first engaging element 102 and a second engaging element 104. When the first engaging element 102 is coupled with the second engaging element 104, an inner diameter is formed which is suited for fitting around a host body canal, i.e., any tube or vessel V within the human or animal body, such as the urethra.

The body fluid flow control device also comprises a locking mechanism 106 for locking the first and second engaging elements 102 and 104 together. The locking mechanism 106 may be of any suitable form. In the illustrated embodiment, locking mechanism 106 is in the form of locking pins 108 located on the first engaging element 102 and locking holes 110 located on the second engaging element 104. In the illustrated embodiment, two locking holes 110 are provided on each side of engaging element 104. Each locking pin 108 is capable of being attached to either of the locking holes 110. The inner diameter formed between parts 102 and 104 may thus be adjusted for use with different sized vessels. It should be understood that any other equivalent locking mechanism can be used for this purpose. Alternative locking mechanisms contemplated by the present invention include, but are not limited to, the use of a strap and snap pins or interconnecting molding on the first and second engaging elements 102 and 104.

The body fluid flow control device of the present invention preferably further includes a piston-like or plunging member 112 located within the inner diameter formed by the coupling of the first and second engaging elements 102 and 104 such that the plunging member 112 may apply pressure against a body canal or vessel, such as a urethra. As can be seen most clearly from FIGS. 2 and 15, plunging member 112 may have a curved profile such that only outer edges of the plunging member contact the vessel surface in use. This substantially reduces the likelihood of necrosis of the tissue of the vessel because it allows pressure to be placed on the vessel over a smaller area than would be possible with a flat plunging member. The curved profile of plunging member 112 may be provided on a removable plunger head, so that a surgeon may select an appropriately sized plunger head for the size of the vessel.

It should be appreciated that the fluid flow control device may take other forms than that illustrated. For example, instead of a plunging member provided in two engagement members, one of the engagement members could be moveable with respect to the other to compress the vessel in order to restrict fluid flow therein. Alternatively, a fluid flow control device in the form of an artificial external annular sphincter or other means for compressing the vessel may be applied to the vessel.

Apertures 113 may be provided in first engaging element 102. The apertures 113 permit tissue growth therethrough from and to the surface of the vessel in order to anchor the body fluid control device onto the vessel. Further apertures (not shown) may be provided to allow dissolvable sutures to be used to secure the engaging element to the vessel on a temporary basis, until the engaging element is completely anchored in place by the tissue growth. Alternatively, the material of the engaging element may be such as to allow suturing therethrough, or the engaging element may be otherwise attached to the vessel. It has been found that tissue growth is achieved within a few weeks of implantation of the device into a host body and so it may also be possible to implant the device without any form of attachment to the vessel, and to simply let the tissue growth firmly attach the device to the vessel over time.

All components of the device are made from biologically inert and compatible materials. For example, the fluid flow control device may be made of polypropylene, silicone, titanium, stainless steel and/or Teflon.

An actuating member is utilized by the body fluid flow control device of the present invention to bias the plunging member 112 to apply pressure against the body vessel when the body fluid flow control device is in the closed position, and to pull the plunging member 112 away from the vessel to open the device. The actuating member may comprise a cable 114 covered by a protective sleeve or sheath 116, the cable 114 having a first end 118 and a second end 120. Cable 114 is preferably a braided stainless steel cable, although any suitable material may be used. Protective sleeve 116 is preferably made from a bio-compatible material having non-stick properties to discourage tissue growth thereon. A suitable material is Teflon. The cable 114 may be slidably moveable within sleeve 116, or cable 114 and sleeve 116 may be slidably moveable together.

The first end 118 of the cable 114 runs slidably through an aperture (not shown) in the second engaging element 104 and is attached to the plunging member 112. A collar 122 is provided around the sleeve 116 where it passes through the aperture in the second engaging element 104, in order that any tissue growth on and around second engaging element 104 does not interfere with the movement of sleeve 116 through the aperture, if the sleeve 116 is designed to move with cable 114. If cable 114 is slidably moveable within sleeve 116, collar 122 prevents tissue ingress into the end of sleeve 116.

FIGS. 5-9 illustrate a control box for the fluid flow control device that is connected to end 120 of cable 114. The control box comprises a housing 202, a motor 204 having a worm gear 206, a spring 208 and bellows 210 to provide a seal around sleeve 116. The housing 202 may be made of polypropylene or any other suitable biologically inert material. Batteries 212 are also provided, which should preferably be suitable for implantation in the body, such as batteries manufactured by Wilson Greatbatch Ltd, of Clarence, N.Y., USA. An operating mechanism (not shown) may be provided in the control box, or may be implanted separately in the host body in an easily accessible place.

The arrangement of the control box and cable 114 allows the control box to be implanted in the body separately from the fluid flow control device. For example, the control box may be implanted close to the patient's skin in their abdomen, with the cable 114 and sleeve 116 extending from the control box 202 to the fluid flow control device that is implanted around the urethra or other body vessel.

Cable 114 is attached at end 120 to a nut 216 which is located in the interior of a slidably moveable casing 214 in housing 202. Spring 208 is also located within casing 214, which has a threaded aperture 218 to allow worm gear 206 to pass into the interior of casing 214.

Figure 9:
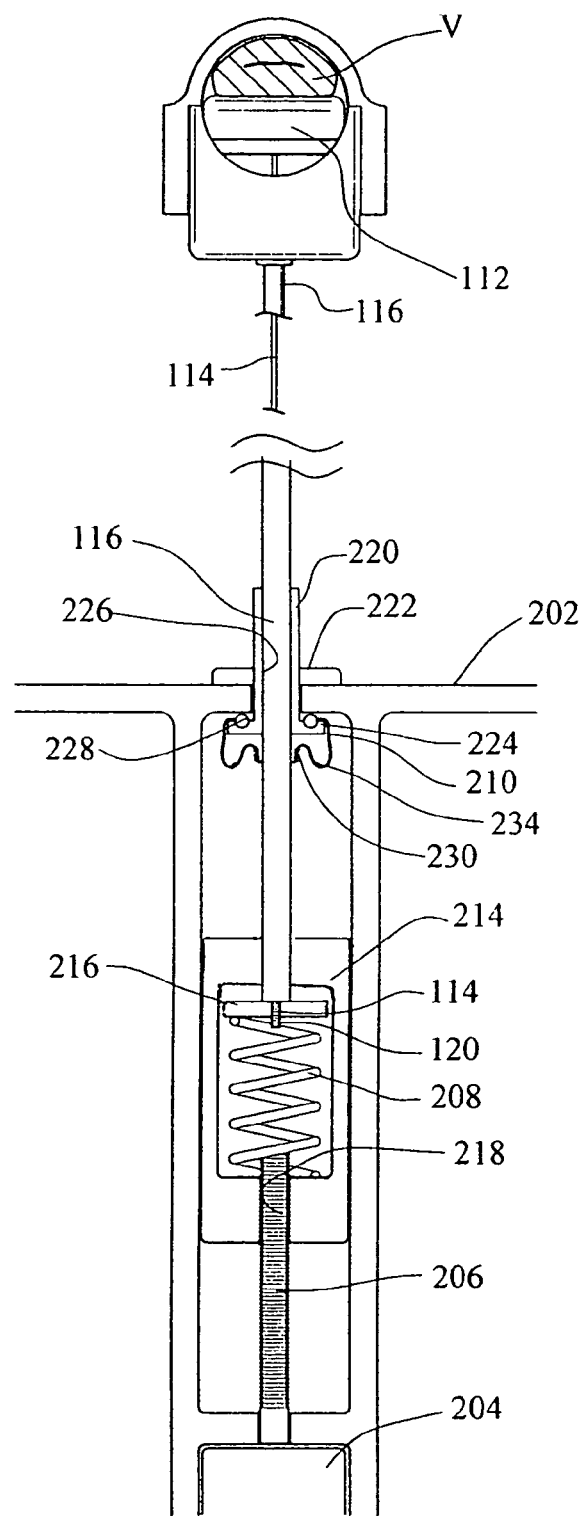
FIG. 9 is a partial cross-sectional view of the motorized activating member of FIG. 7 in the closed position.

Spring 208 is interposed between the motor 204 and cable 114 in order to provide a coupling for selectively transmitting axial movement from the motor 204 to the cable 114 and hence to the body vessel V, the operation of which is described with reference to FIGS. 7 to 9 below. In the illustrated embodiment, the motor 204 acts on casing 214 to move spring 208 and cable 114 by means of the nut 216. However, any suitable compressible member may be used in the casing 214 to cushion the vessel from the action of the motor, for example, a resiliently deformable material may be used, or a compressible fluid such as a gas could be used if casing 214 was suitably sealed. Alternatively, a spring or other compressible member may be connected directly to or inserted in cable 114. Such an arrangement would preferably use a compressible member that was stiff enough so that pushing and pulling motions were still imparted to the cable 114 on operation of the motor.

The slidable casing 214 and worm gear 206 allow axial movement to be imparted to cable 114 by motor 204, but it should be appreciated that any suitable axial actuation of cable 114 may be used. For example, the motor 204 may have an axially moveable actuator, or suitable gearing could be provided to act on a toothed rack or other axially moveable element. Alternatively, the cable could have a flexible end that may be wound around an axle in housing 202.

The sleeve 116 containing cable 114 should be sealed to housing 202 to prevent ingress of body fluids from damaging the motor and other components of the control box. Any suitable seal may be used, but it should be noted that where sleeve 116 is designed to be slidably moveable, it is not possible to seal tightly around sleeve 116, as the sleeve needs to be axially moveable in order to impart movement to plunging member 112. One method of sealing sleeve 116 to housing 202 is to use a bellows mechanism. A suitable bellows mechanism 210 is illustrated in FIGS. 7-9. Bellows 210 is designed so that as sleeve 116 moves axially, bellows 210 expands or collapses in on itself so that fluid that seeps into housing 202 around sleeve 116 is captured by bellows 210, and can be forced back out of the housing 202 when the device is moved to a closed position.

The sleeve 116 may be sealed to bellows 210 and housing 202 by means of a threaded bolt 220, and a nut 222. Bolt 220 is passed through an aperture in housing 202 with its head 224 in the interior of the housing. Sleeve 116 passes through and is a close fit with a central bore 226 in bolt 220. Bellows mechanism 210 is generally tubular and is sealed to the underside of head 224 of bolt 220 by an O-ring seal 228. As the nut 222 is tightened on bolt 220, compression of the O-ring seal 228 causes a tight seal to prevent ingress of fluid into housing 202 around the exterior of bolt 220. Bellows 210 extends around the head 224 of bolt 220 and is sealed to sleeve 116 in the interior of housing 202 by a tightly wound spring 230. The spring 230 may be placed onto the bellows 210 before the sleeve 116 is forced through the bellows 210 and spring 230 in order to obtain the tightest seal possible. Other methods of sealing bellows 210 to sleeve 116 include cable clamps, C-clips, adhesive, etc. A reinforcing ring 234 is provided on one surface of bellows 210, to ensure that the bellows 210 collapses correctly as the sleeve 116 is moved axially. The reinforcing ring 234 may be a thickened area in the wall of the bellows 210, or may be a separate ring that is attached to the bellows, by gluing or any other suitable means. Instead, or in addition to, the reinforcing ring 234, the bellows may be pleated or folded in order to ensure correct folding when the fluid flow control device is moved to the closed position.

It should be noted that bellows 210 can be of any suitable shape, provided that a seal is made at the housing and around the sleeve, and that bellows allows movement of the sleeve into and out of the housing. For example, bellows 210 may be a simple tubular shape, with ends of the tube being sealed to the housing and sleeve. Alternatively, bellows 210 may be of a frusto-conical shape, or a more complicated shape such as a bell-shape or could be folded or pleated. The seal to the housing could be close to the aperture in the housing through which the seal extends, as illustrated, either inside the housing or outside the housing. Alternatively, the seal could be made to the wall of the housing, around or behind the bolt 220.

It is possible to seal the sleeve 116 and the housing 202 without using a bellows mechanism, but it has been found that energy losses are created as movement of the sleeve 116 creates friction against the seal. This can cut the battery life of the motor by up to $\frac{1}{3}$. For example, a flexible annular ring may be sealed between the sleeve 116 and the housing 202, the annular ring stretching as the sleeve is axially moved.

Alternatively, a series of seals may be provided along sleeve 116, each seal preventing some fluid ingress to housing 202.

Control circuitry (not shown in FIGS. 7-9) is provided, which operates the motor on receipt of a signal from an operating mechanism. Any of the several well-known control devices can be used to control the operation of the body fluid flow control devices of the present invention by a user so long as the objectives of the present invention are not defeated. Suitable operating mechanisms include radio-control devices, or a magnetic devices that can be sensed by the control circuitry. With a magnetic device, the user may be provided with a separate magnet that they carry with them, and which they position adjacent the skin over the implanted switch when they wish to operate the device. The magnet may be of any suitable shape, and may be shaped for example like a pen or credit card so that its purpose is not immediately apparent to other people. The magnet should have a weak magnetic field so that it must be placed close to the switch in order to operate the device, in order to prevent accidental operation of the device if the magnet is carried in a pocket. Alternatively, a touch sensor, infrared, voice or sound activation may be used, or a manually operated switch may be implanted under the skin of the patient.

A remotely operated operating mechanism is preferred because the device can be operated without irritation to the skin, as would happen with a manually operated trigger. In the preferred embodiment, a manual override switch may be provided in addition to the remotely operated triggering mechanism. The manual override switch is designed to be used temporarily if the control box fails and the user is not close to a physician's office or hospital to have the control box changed. The manual override switch may be provided in the control box, and may be sealed from the interior of the control box until the first activation of the switch, for example by a membrane seal. Such a use of the manual override switch may eventually allow fluid ingress into the control box, which may then need to be replaced. Alternatively, no manual override switch may be provided, which would mean that the user would have to use incontinence pads until the control box could be replaced.

The control circuitry controls operation of the motor, and may detect the position of the plunging member, for example, via the position of the casing or via the drag exerted on the motor. Preferably, the control circuitry also monitors the level of charge in the battery. The control circuitry can be used to initiate opening or prevent closing of the fluid flow control device if a problem such as low battery or a defective motor is detected, so that the device can be caused to remain in the open position. For example, once the device has been opened, an abutment (not shown) may be caused to contact the casing 214 to prevent any further movement thereof. The motor may also be shut off. The device may still be operable by a manual override, as the spring 208 can be compressed and allowed to expand within casing 214 to allow movement of the cable 114 to open and close the device.

The control box 202 may also contain components that allow a physician to interrogate the control circuitry by a remote telemetry system without accessing the box itself. Such components may be interrogated and/or controlled by radio waves or other interactive signals transmitted and received by the telemetry system, or any other suitable mechanism. This allows the physician to check the charge in the batteries, any internal sensors, to alter the tension in the cable 114, and to make other suitable adjustments. A pressure sensor may be provided on the plunger 112 to monitor the pressure between the plunger 112 and the vessel V when the plunger is in the closed position. The pressure sensor may also be interrogated by the telemetry system, which can then be used to alter the settings for the control device. For example, the number of turns that the motor 204 causes worm gear 206 to make on each operation of the device may be altered in order to set the correct distance of travel of the cable 114, and hence plunger 112 for any particular patient so as to alleviate any excess pressure exerted on the vessel V. In addition, the telemetry system may include control commands to cause the motor to open and close the body fluid flow control device, either as an override system to the normal operating means, or in addition to the normal operating means in order to test the device in situ.

If the control box causes the device to fail or remain in the open position if a problem is detected, this will simply mean that the patient will return to the condition that they were in before implantation of the device, in other words, in a condition of incontinence. If the device failed in the closed position, the patient would need to be catheterized. However, a manual override system would allow the patient to operate the system manually for a considerable period of time or until medical aid was obtainable.

Actuation of the device is described with reference to FIGS. 7 to 9. In the open position shown in FIG. 7, the motor 204 has operated the worm gear 206 to draw casing 214 towards the motor 204. This pulls nut 216 along with the casing 214, and thus acts on cable 114 to pull the plunging member 112 away from the vessel V. Bellows 210 is also at its fully extended position. In order to close the fluid control device, the motor 204 is activated to turn worm gear 206 in the opposite direction to that used to open the device. As worm gear 206 is operated, casing 214 is moved away from the motor 204, spring 208 pushing on nut 216 to bias plunging member 112 against the vessel V, as shown in FIG. 8. As the motor 204 is operated further, the vessel V prevents plunger 112 moving, and prevents movement of cable 114 and hence nut 216, due to the increased force needed to move cable 114 against the vessel V when the vessel V is already closed. Nut 216 presses against spring 208, causing compression of the spring 208, as shown in FIG. 9. It can thus be seen that any further movement of worm gear 206 by motor 204 does not result in compression and injury of the vessel V, but the further compression of spring 208. In this way, axial movement of casing 214 may be selectively transmitted to cable 114. This protects the vessel V against failure of the device by continuous running of the motor 204, as the vessel cannot be further compressed due to the interplay between the vessel V and the spring 208.

An alternative embodiment of the control box is illustrated in FIGS. 10 and 11. The control box comprises a housing 902, a motor 904 having a worm gear 906, a spring 908 and bellows 910. Batteries 912 are also provided, along with control circuitry (not shown). The spring 908 is located in a slidable spring casing 914. An operating mechanism (not shown) may be provided in the control box, or may be implanted separately in the host body in an easily accessible place. The spring, worm gear and motor arrangement are as described for FIGS. 5-9, and will not be further described.

Housing 902 is preferably formed in two pieces, a main body 916 and an end lid 918. End lid 918 includes a lip 920 that fits inside an end 922 of main body 916. A groove 924 is provided around lip 920, in order to receive an O-ring 926. End lid 918 is also sonically welded to main body 916 in order to provide a good seal. A groove 928 is provided around the exterior of end 922 of main body 916, in order to allow for ease of removal of lid 918 with a suitable tool when necessary. An interior housing 930 extends along the length of housing 902, to one side thereof, in order to separate the motor 904, worm gear 906, slidable casing 914, bellows 910 and other moveable parts from the batteries 912. Interior housing 930 has a flange 932 at an end 934 remote from end 922 of main body 916, with an O-ring groove 936 provided in flange 932. A set screw 938 is also provided in interior housing 930, in order to lock motor 904. Electrical contacts 940 extend to motor 904 from end lid 918. An internally directed collar 942 having an internal thread extends around flange 932 within housing 902, and interior housing 930 is secured into housing 902 by means of an externally threaded nut 944 which is screwed into place to hold flange 932 in position. Nut 944 may have pin holes 946 to allow for tightening thereof. An externally directed collar 948 having an internal thread is also provided in housing 902, in order to allow the cable 114 to pass into interior housing 930.

Sleeve 116 has an end 950 which is attached to a hollow connector 952 having a first end 954 and a second end 956. At end 954, connector 952 has backwardly-directed teeth 958 around the circumference thereof which attach to the inside of sleeve 116 adjacent to end 950, and act to prevent sleeve 116 from being pulled loose. The second end 956 of connector 952 has an external thread 960, as well as a groove 962 suitable for receiving an O-ring 964. Thread 960 is screwed into the internal thread provided within collar 948 on housing 902. Cable 114 extends into housing 902 through connector 952, and is attached at its end 120 to a link member 966 which extends into casing 914 and terminates in nut 216. The connection between cable 114 and link member 966 is shown enlarged in FIG. 11. The cable end 120 is fitted into a connector piece 968 that has a tapered end 970 and a groove 972 for receiving a sealing ring. Link member 966 has an opening 974 for receiving connector piece 968, opening 974 having an internal shoulder 976. A metal O-ring 978 is received by shoulder 976 and is held in place by a ring retainer 980. Connector piece 968 is pushed into opening 974 until the metal O-ring 978 seats in groove 972 to form a seal between connector piece 968 and link member 966.

Bellows 910 are attached to housing 902 by means of nut 944 screwed into inwardly directed collar 942. Bellows 910 has an end flange 982, which extends adjacent to flange 932 of interior housing 930, and has an integral O-ring 984 to seal in O-ring groove 936 of flange 932 so that bellows 910 is tightly sealed to housing 902 by interior housing 930. Bellows 910 is also attached to cable link member 966 by means of a cable link 986, and has a pleated conical shape above flange 982 so that it may fold easily when compressed. It should be noted that in the embodiment of FIG. 10, the bellows 910 is not attached to the sleeve 116, as the sleeve 116 is not axially moveable. Instead, cable 114 is axially moveable within sleeve 116. In this embodiment, bellows 910 may not be necessary, as a good seal may be provided between connector 952 and control box 902. However, it is advantageous to provide an additional seal, for example using bellows 910, to prevent fluid ingress into control box 902.

The operation of the control box of FIG. 10 is the same as for the control box of FIGS. 5 to 9, and will not be further described.

Figure 12:
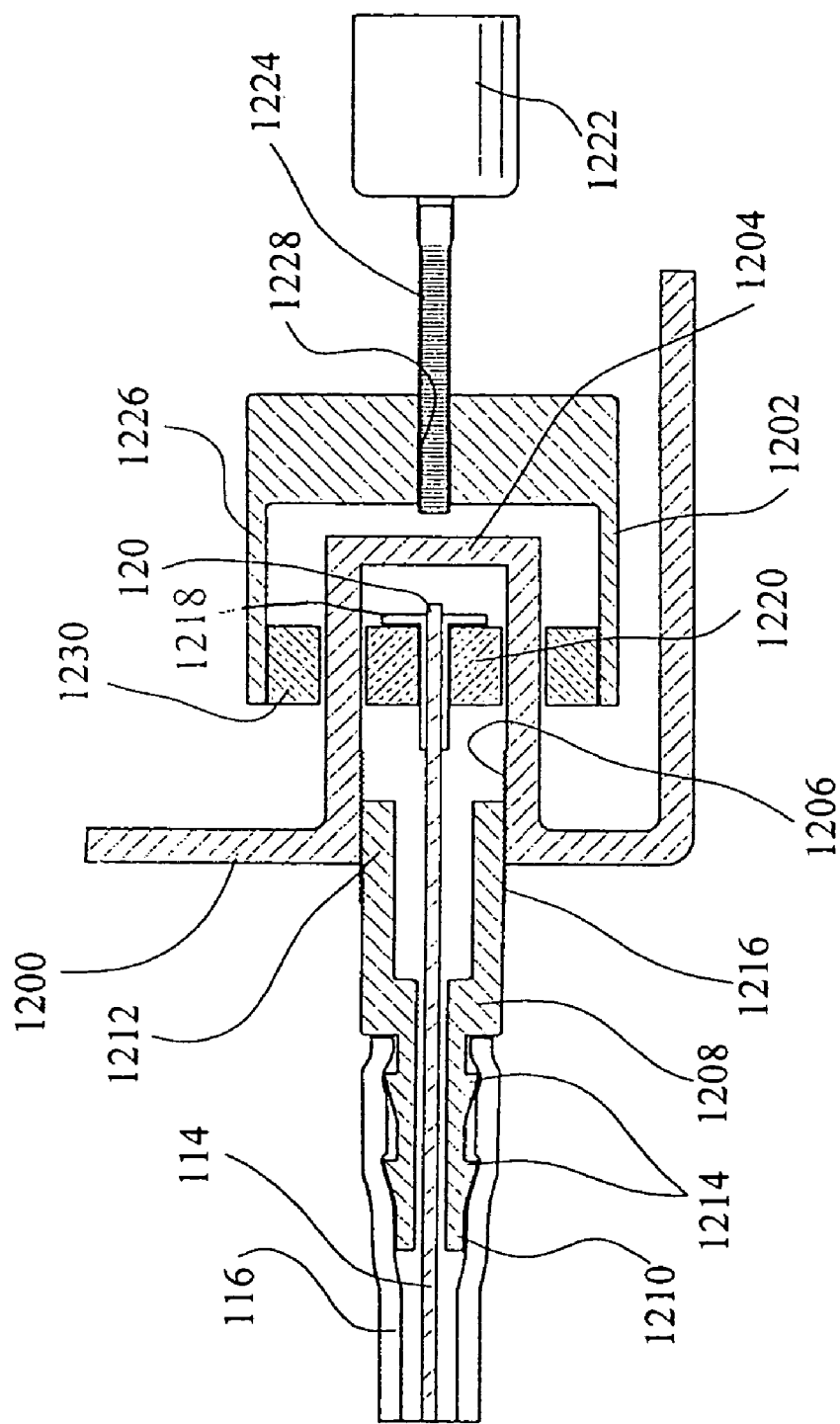
FIG. 12 is a partial cross-sectional view of an alternative embodiment of motorized actuating member.

A further alternative embodiment of a seal for the sleeve and an actuator for the cable is illustrated in FIG. 12. In the illustrated embodiment, control box 1200 is completely sealed so that no fluid ingress into the box can take place. A hollow cylindrical bore 1202 that is sealed at one end 1204 is formed in control box 1200. Bore 1202 has internal threads 1206 provided adjacent an outer surface of control box 1200.

An end of sleeve 116 is attached to a hollow connector 1208, connector 1208 having an end 1210 and an end 1212. End 1210 of connector 1208 is dimensioned to pass into the end of sleeve 116, connector 1208 having outwardly and rearwardly directed teeth 1214 at end 1210 to engage the interior of sleeve 116, thereby securing connector 1208 to sleeve 116. End 1212 of connector 1208 is dimensioned to be slightly larger in diameter than sleeve 116, and has external threads 1216. Connector 1208 may be screwed into bore 1202 of control box 1200 by means of threads 1216 and 1206.

End 120 of cable 114 is located in bore 1202, and is provided with a collar 1218. An annular magnet 1220 is supported by collar 1218 around end 120 of cable 114. Cable 114 is axially moveable within sleeve 116, and therefore a bellows seal is not necessary around sleeve 116. In addition, as sleeve 116 is not moveable, tissue growth around the sleeve cannot affect the operation of the device.

A motor 1222 has a threaded worm gear 1224 engaged with a casing 1226 through a screw-threaded aperture 1228 located in the bottom of the casing. Casing 1226 extends around bore 1202, and an annular magnet 1230 is supported around the interior of an upper edge of casing 1226. Magnet 1230 is aligned with magnet 1220 located on end 120 of cable 114.

In order to actuate cable 114 to open and close the fluid flow control device, the motor 1222 operates the worm gear 1224, which moves casing 1226 along the exterior of bore 1202. Magnet 1230 acts through the plastic material comprising bore 1202, and causes magnet 1220 to track its movement. This in turn causes cable 114 to be axially moved, operating the fluid flow control device. If the motor 1222 continues operating the worm gear 1224 towards the cable 114 when the body vessel has already been closed, the attraction of magnet 1220 for magnet 1230 is not enough to cause the cable 114 to be moved further, due to resistance from the vessel walls, thus preventing potential damage to the vessel. Thus, axial movement of casing 1226 is selectively transmitted to cable 114. In addition, the casing 1226 will come to rest against bore 1202 or an interior surface of control box 1200, preventing the magnets from getting too far out of alignment.

It should be appreciated that a magnetic link between the motor and cable may be achieved in many ways other than that illustrated in FIG. 12. For example, the magnets need not be annular, but could be placed to one side of the cable. In addition, the magnets need not operate by mutual attractions, but could work by repelling each other to close the vessel, with a spring action or other means operating to open the vessel once the motor-driven magnet was pulled back towards the motor. With a repelling action, magnets could be placed directly on the ends of the cable and an axially movable actuator driven by the motor.

Figure 13:
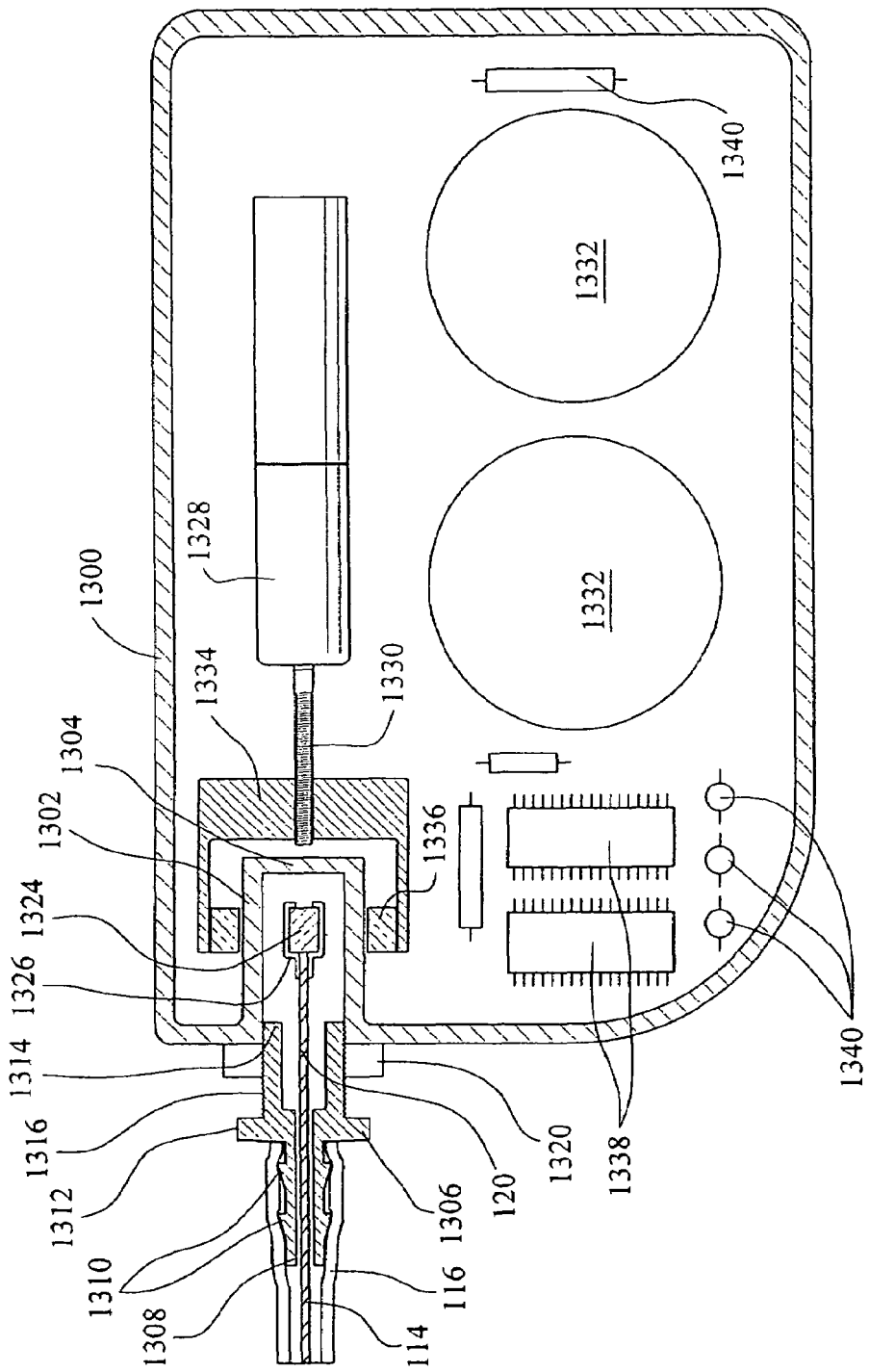
FIG. 13 is a top partial cross-sectional view of yet a further alternative embodiment of control box and device.

An alternative embodiment of a magnetic coupling for selectively transmitting axial movement to the cable is illustrated in FIGS. 13 and 14. These figures illustrate a control box 1300 that is completely sealed. A bore 1302 having a blind end 1304 is provided in the control box 1300 for receiving the end 120 of cable 114. A connector 1306 is used to connect sleeve 116 to bore 1302. The connector 1306 has a first end 1308 with rearwardly directed teeth 1310, a central shoulder 1312 and a second end 1314 having external screw threads 1316. End 1308 of connector 1306 is pushed into the end of sleeve 116, the teeth 1310 acting on the inner surface of the sleeve. End 1314 of connector 1306 is connected to control box 1300 by means of an O-ring seal 1318 and an internally threaded nut 1320 which is threaded onto threads 1316. Nut 1320 is welded at 1322 to the control box 1300 to form a tight seal.

The cable 114 extends into bore 1302. A cylindrical magnet 1324 is attached to end 120 of cable 114 by a collar 1326 which is deformed onto the magnet 1324 and cable end 120 for a tight fit. The control box 1300 includes a motor 1328, a worm gear 1330 and batteries 1332 as described for the FIG. 10 embodiment. A casing 1334 having an annular magnet arrangement 1336 is threaded onto worm gear 1330, and operates in the same manner as in the FIG. 10 embodiment so will not be further described. Control circuitry including IC's 1338 and other standard components 1340 including resistors and capacitors are also shown.

FIG. 15 illustrates an embodiment of a connector joining first end 118 of cable 114 to the body fluid control device. Connector 1500 has a first end 1502 having outwardly directed teeth 1504 which grip into the inner surface of sleeve 116. A second end 1506 of connector 1500 has a collar with inwardly directed threads 1508 which are threaded onto outwardly directed threads 1510 on a collar 1512 attached to the body fluid flow control device. An O-ring 1514 forms a tight seal to the collar 1512.

FIG. 15 also illustrates plunger 112 in detail. Plunger 112 includes a perforated metal bracket 1516 attached to a metal collar 1518. The main body of plunger 112 is formed of silicon that is molded onto the perforated bracket 1516, the silicon extending through the perforations in the bracket to form a tight fit between plunger 112, bracket 1516 and collar 1518. Metal collar 1518 may be simply crimped onto end 118 of cable 118.

FIG. 16 illustrates a further alternative method of connecting cable 114 and sleeve 116 to the body fluid flow control device. In the embodiment of FIG. 16, the fluid flow control device has a collar 1600 with internal threads 1602. A connector 1604 is used to connect sleeve 116 to collar 1600. Connector 1604 has external threads 1606, a central collar 1608 and outwardly directed teeth 1610. It should be noted that connector 1604 may be the same as connector 1306 illustrated in FIG. 13. This allows for economies in manufacture, as only one type of connector need be provided for both ends of the sleeve 116. A metal collar 1612 is used to connect the plunger (not shown in FIG. 16) to end 118 of cable 114. An O-ring 1614 may seal between collar 1612 and connector 1604.

It will be understood that various embodiments of the present invention have been disclosed by way of example and that other modifications and alterations may occur to those skilled in the art without departing from the scope and spirit of the appended claims. Thus, the invention described herein extends to all such modifications and variations as will be apparent to the reader skilled in the art, and also extends to combinations and subcombinations of the features of this description and the accompanying figures. Although preferred embodiments of the present invention have been illustrated in the accompanying figures. and described in the foregoing detailed description, it will be understood that the present invention is not limited the embodiments disclosed, but is capable of numerous rearrangements, modifications and substitutions without departing from the spirit of the present invention as set forth and defined by the following claims, such as for example those embodiments described in non-provisional U.S. patent application Ser. No. 09/048,823, filed Mar. 26, 1998, which is incorporated hereinto in its entirety by reference.

The invention claimed is:

1. A remote telemetry system for an implantable apparatus for controlling fluid flow within a host body, the telemetry system comprising:
    a signaling mechanism for sending and receiving signals to and from a control unit implanted in a host body in order to monitor the operation of the implantable apparatus, wherein based on information received from the control unit the telemetry system sends signals to the control unit for altering or maintaining operating settings of the implantable apparatus, said system further comprising at least one sensor to monitor actions of the implantable apparatus on the host body, and a mechanism to interrogate said sensor to permit feedback on the sensed data,
    wherein at least one of said sensors is provided to monitor pressure exerted by a moveable part of said implantable apparatus on a part of said host body, the feedback on the sensed data causing commands to be sent to said control unit to alter or maintain the range of movement or position of said moveable part within the host body.

2. The remote telemetry system of claim 1, wherein said signals are electromagnetic radiation.

3. The remote telemetry system of claim 2, wherein said signals are radio waves.

4. The remote telemetry system of claim 1, further comprising a second sensor for sensing a battery charge level.

5. The remote telemetry system of claim 1, wherein said system provides for an override control command to open and/or close the implantable apparatus.

6. The remote telemetry system of claim 1 wherein the implantable apparatus is adapted for controlling fluid flow in a urethra of the host body and said sensor senses and provides feedback on the amount of pressure the movable part places on the urethra.

7. The remote telemetry system of claim 1 wherein said movable part maintains the body part of the host body in a continuous normally closed position until directed by the control unit to temporarily open.

8. A remote telemetry system for an implantable apparatus for controlling fluid flow of a body canal or vessel within a host body, the telemetry system comprising:
    an implantable apparatus having a control unit and a movable part, said control unit and said movable part implanted within a host body, said control unit directing the position of said movable part within the host body, wherein in a body canal or vessel closed position said movable part is adapted to contact and apply pressure to a body canal or vessel within the host body;
    a signaling mechanism for sending and receiving signals to and from the control unit in order to monitor the operation of the implantable apparatus, wherein based on information received from the control unit the telemetry system sends signals to the control unit for altering or maintaining operating settings of the implantable apparatus, said system further comprising at least one sensor to monitor actions of the implantable apparatus on the host body, and a mechanism to interrogate said sensor to permit feedback on the sensed data,
    wherein at least one of said sensors is provided to monitor pressure exerted by the moveable part on the body canal or vessel of said host body, the feedback on the sensed data causing commands to be sent to said control unit to alter or maintain the range of movement or position of said moveable part within the host body.

9. The remote telemetry system of claim 8, wherein said signals are electromagnetic radiation.

10. The remote telemetry system of claim 8, wherein said signals are radio waves.

11. The remote telemetry system of claim 8, further comprising a second sensor for sensing a battery charge level to determine whether a command should be sent to release pressure on the body canal or vessel by the movable part such that the body canal or vessel is an at least partially open position.

12. The remote telemetry system of claim 8, wherein said system provides for an override control command to open and/or close the implantable apparatus.

13. The remote telemetry system of claim 8 wherein the body canal or vessel is a urethra within the host body and said implantable apparatus is adapted for controlling fluid flow in the urethra of the host body; wherein and said sensor senses and provides feedback on the amount of pressure the movable part places on the urethra.

14. The remote telemetry system of claim 8 wherein said movable part maintains the body canal or vessel of the host body in a continuous normally closed position until directed by the control unit to temporarily open.

15. A remote telemetry system for an implantable apparatus for controlling fluid flow of an urethra in a host body, the telemetry system comprising:

an implantable apparatus having a control unit and a movable part, said control unit and said movable part implanted within a host body, said control unit directing the position of said movable part within the host body, wherein in an urethra closed position said movable part is adapted to contact and apply pressure to the urethra;

a signaling mechanism for sending and receiving signals to and from the control unit in order to monitor the operation of the implantable apparatus, wherein based on information received from the control unit the telemetry system sends signals to the control unit for altering or maintaining operating settings of the implantable apparatus, said system further comprising a first sensor to monitor pressure exerted by the movable part on the urethra, a second sensor for sensing a battery charge level to determine whether a command should be sent to release pressure on the urethra by the movable part such that the urethra is an at least partially open position, and a mechanism to interrogate said first sensor to permit feedback on the sensed data from provided by said first sensor;

wherein the feedback on the sensed data causing commands to be sent to said control unit to alter or maintain the range of movement or position of said moveable part with respect to the urethra;

wherein said movable part adapted to maintain the body canal or vessel of the host body in a continuous normally closed position until directed by the control unit to temporarily open.

16. The remote telemetry system of claim 15, wherein said signals are electromagnetic radiation.

17. The remote telemetry system of claim 15, wherein said signals are radio waves.

18. The remote telemetry system of claim 15, wherein said system provides for an override control command to instruct the control unit to position the movable part such that the urethra is at least partially opened to permit fluid flow.

* * * * *